US011890400B2

(12) United States Patent
Erlenkoetter et al.

(10) Patent No.: US 11,890,400 B2
(45) Date of Patent: Feb. 6, 2024

(54) DEVICE AND METHOD FOR DETERMINING RESIDUAL BLOOD IN A DIALYZER AND DIALYSIS SYSTEM

(71) Applicant: FRESENIUS MEDICAL CARE DEUTSCHLAND GMBH, Bad Homburg (DE)

(72) Inventors: Ansgar Erlenkoetter, St. Wendel (DE); Lukas Utzig, St. Wendel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 799 days.

(21) Appl. No.: 17/043,709

(22) PCT Filed: Apr. 9, 2019

(86) PCT No.: PCT/EP2019/058919
§ 371 (c)(1),
(2) Date: Sep. 30, 2020

(87) PCT Pub. No.: WO2019/197387
PCT Pub. Date: Oct. 17, 2019

(65) Prior Publication Data
US 2021/0060225 A1 Mar. 4, 2021

(30) Foreign Application Priority Data
Apr. 10, 2018 (DE) .................... 10 2018 205 387.1

(51) Int. Cl.
*A61M 1/16* (2006.01)
*G16H 20/17* (2018.01)
(Continued)

(52) U.S. Cl.
CPC ........ *A61M 1/1601* (2014.02); *A61M 1/1633* (2014.02); *A61M 1/1672* (2014.02);
(Continued)

(58) Field of Classification Search
CPC .............. A61M 1/1601; A61M 1/1633; A61M 1/1672; G16H 20/17; G16H 30/40; G16H 40/63
(Continued)

(56) References Cited

U.S. PATENT DOCUMENTS

| 2011/0120932 A1* | 5/2011 | Buck | B01D 63/02 428/34.1 |
| 2012/0170020 A1* | 7/2012 | Bado | G01N 21/251 210/85 |

(Continued)

FOREIGN PATENT DOCUMENTS

| CN | 1970099 A | 5/2007 |
| DE | 102013103335 A1 | 10/2014 |

(Continued)

OTHER PUBLICATIONS

Office Action issued in corresponding Indian Patent Application 202017040009 dated Jul. 25, 2022 (with English translation) (6 pages).
(Continued)

*Primary Examiner* — Michael R Neff
(74) *Attorney, Agent, or Firm* — Kilyk & Bowersox, P.L.L.C.

(57) ABSTRACT

The present invention relates to a device (1) and a corresponding method for determining residual blood in a dialyzer (2) comprising a holding device (6) configured to accommodate a dialyzer (2), an image capturing device (7) configured to capture at least one image of a dialyzer (2) accommodated by the holding device (6), in particular a filter (4) located in the dialyzer (2), and generate corresponding image data having a plurality of image points, each of which assigned at least one respective intensity value, in particular a color value, and a control device (9) configured to determine residual blood information characterizing the presence and/or content of residual blood in the dialyzer (2) on the basis of a statistical frequency of at least a portion of the intensity values in the at least one image. The invention further relates to a dialysis system having such a device (1).

20 Claims, 3 Drawing Sheets

Figure 1:
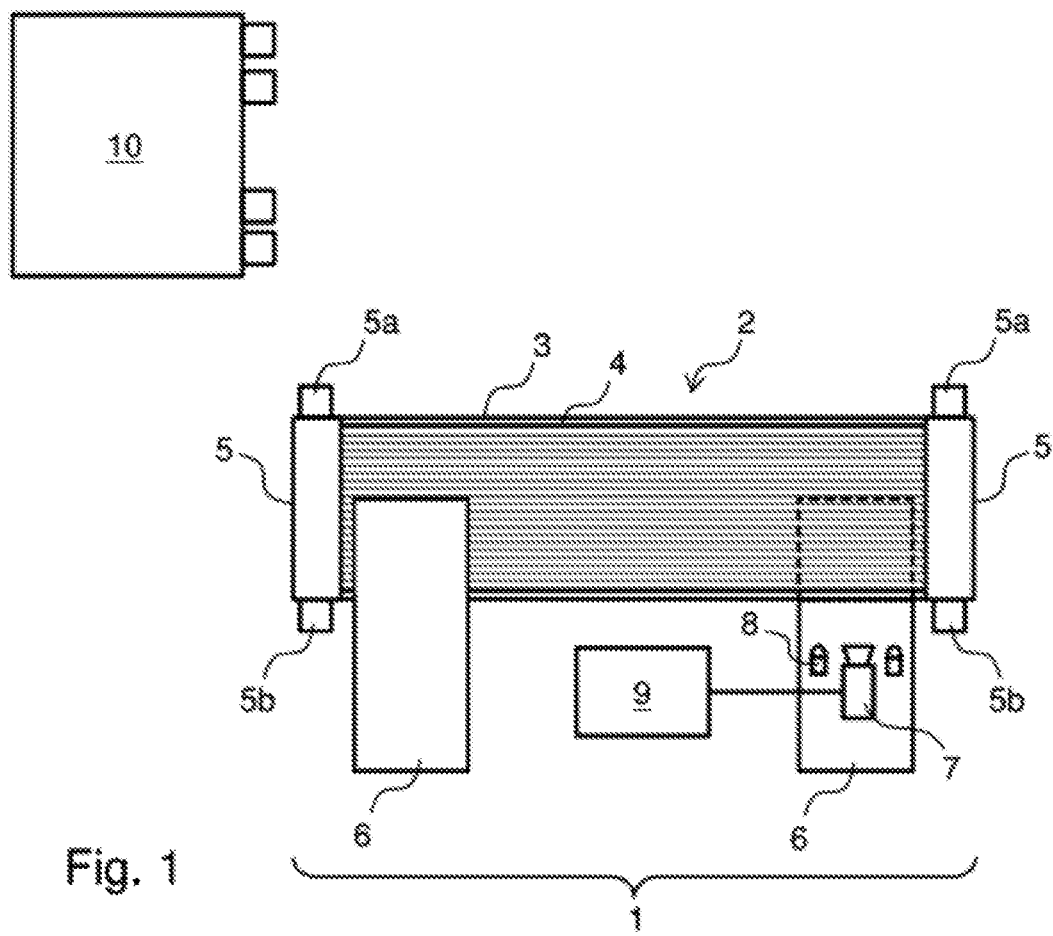

(51) Int. Cl.
*G16H 30/40* (2018.01)
*G16H 40/63* (2018.01)

(52) U.S. Cl.
CPC ............ *G16H 20/17* (2018.01); *G16H 30/40* (2018.01); *G16H 40/63* (2018.01)

(58) Field of Classification Search
USPC ........................................................ 382/128
See application file for complete search history.

(56) References Cited

U.S. PATENT DOCUMENTS

| | | |
|---|---|---|
| 2015/0294461 A1 | 10/2015 | Satish et al. |
| 2016/0058934 A1 | 3/2016 | Strohhofer et al. |

FOREIGN PATENT DOCUMENTS

| | | | |
|---|---|---|---|
| EP | 1078642 | A2 | 2/2001 |
| EP | 2322907 | A1 | 5/2011 |
| JP | 2004081833 | A | 3/2004 |
| JP | 2004113894 | A | 4/2004 |
| JP | 2013500800 | A | 1/2013 |
| JP | 2017521640 | A | 8/2017 |

OTHER PUBLICATIONS

International Preliminary Report on Patentability issued in corresponding International Patent Application No. PCT/EP2019/058919 (English translation) dated Oct. 22, 2020 (6 pages).

International Search Report and Written Opinion issued in corresponding International Patent Application No. PCT/EP2019/058919 (with English translation of International Search Report) dated Jul. 2, 2019 (9 pages).

Office Action issued in corresponding Japanese Patent Application 2020-554480 dated May 1, 2203 (with English translation) (4 pages).

* cited by examiner

DEVICE AND METHOD FOR DETERMINING RESIDUAL BLOOD IN A DIALYZER AND DIALYSIS SYSTEM

This application is a National Stage Application of PCT/EP2019/058919, filed Apr. 9, 2019, which claims priority to German Patent Application No. 10 2018 205 387.1, filed Apr. 10, 2018.

The present invention relates to a device and a method for determining residual blood in a dialyzer as well as a dialysis system.

For cleansing a patient's blood, dialysis systems are known in which a filter made of a plurality of hollow fibers, their wall being formed by a semipermeable membrane, is arranged in a so-called dialyzer. While blood is conducted through the fibers, a so-called dialysate flows through the exterior space so that small mole-cules such as for instance water, electrolytes and uremic substances from the blood can pass through the membrane into the dialysate and then be removed.

In dialysis, an unwanted stimulation of blood coagulation can be prevented or at least decreased by using an anticoagulant (e.g. heparin). If the anticoagulant dose is too low, clots can form during the treatment. These clots can block individual or also many of the hollow fibers. When the blood is returned again to the patient at the end of the treatment, it can happen that a certain amount of blood, also known as "residual blood," remains in the respective fibers and is not returned to the patient.

There are various methods used in clinical practice to determine the optimal anticoagulant dose. One possibility is determining coagulation times (e.g. ACT=activated clogging time, aPTT=activated partial thromboplastin time) from blood samples taken during the treatment (e.g. at t=60 min). A prolonged coagulation time indicates too high of an anticoagulation dose having been selected, a reduced coagulation time in contrast too low of a dose. Furthermore, also the bleeding time required for the patient to stop bleeding after removal of the needle can be used to estimate the optimal anticoagulant dose.

Last but not least, technical personnel can examine the so-called "streaking" of used filters. When a filter is substantially white at the end of the reinfusion, non-blocked free fibers are white while those blocked by residual blood are red. Examining filters can however result in a very subjective assessment such that different persons can come to different conclusions and results.

It is an object of the invention to specify a device and a method for reliably determining residual blood in a dialyzer as well as a corresponding dialysis system.

A device according to the invention for determining residual blood, in particular blood clots, in a dialyzer comprises: a holding device configured to accommodate a dialyzer, an image capturing device configured to capture at least one image of a dialyzer accommodated by the holding device, in particular a filter located in the dialyzer, and generate corresponding image data having a plurality of image points (pixels), each of which assigned at least one respective intensity value, in particular a color value, and a control device configured to determine residual blood information characterizing the presence and/or content of residual blood in the dialyzer on the basis of a statistical frequency of at least a portion of the intensity values in the at least one image.

A dialysis system according to the invention comprises the device according to the invention as well as a dialysis device able to be connected to a dialyzer by tubes and configured to conduct blood and dialysate through the dialyzer to cleanse the blood.

A method according to the invention for determining residual blood, in particular blood clots, in a dialyzer comprises the following steps: capturing at least one image of a dialyzer, in particular a filter located in the dialyzer, and generating corresponding image data having a plurality of image points (pixels), each of which assigned at least one respective intensity value, in particular a color value, and determining residual blood information characterizing the presence and/or content of residual blood in the dialyzer on the basis of a statistical frequency of at least a portion of the intensity values in the at least one image.

One aspect of the invention is based on the approach of a camera capturing one or more images of the filter located in the dialyzer and detecting or respectively determining the presence and/or content of any residual blood in the filter, in particular coagulated blood (so-called blood clots), by analyzing at least a portion of the gray and/or color values of the captured image or images in terms of their statistical frequency within the respective image and deriving therefrom corresponding residual blood information indicating whether or respectively how much residual blood is present in the filter. The analyzed statistical frequency of the grey values or respectively color values in the image can relate to absolute frequency values indicating the number of respective gray values or respectively color values of a specific level appearing in the image. Alternatively or additionally, the analyzed statistical frequency can relate to relative frequency values, representing a measure of the ratio of the respective gray values or respectively color values of a specific level appearing in the image to the total number of gray values or respectively color values appearing and/or possible in the image.

The automated analysis of filter images captured by the camera using statistical methods enables an objective and thus particularly reliable determination of any residual blood in a dialyzer. A further advantage of the invention also lies in being able to particularly reliably determine or respectively optimize an anticoagulant dosage amount on the basis of the residual blood information as thereby determined.

Preferably, the image capturing device is configured to capture electromagnetic radiation at one or more different wavelengths or wavelength ranges and generate intensity values, in particular two or more color values, for each of the wavelengths or respectively each of the wavelength ranges per each image point. The control device is thereby further configured to determine the residual blood information on the basis of a statistical frequency of the intensity values for one or more of the wavelengths or respectively for one or more of the wavelength ranges respectively in the at least one image. Preferably, the image capturing device has a so-called color channel for each of the different wavelengths or respectively each of the different wavelength ranges in which a corresponding color value is determined for each image point. Preferably, the image capturing device has three color channels for the wavelengths or respectively wavelength ranges of red, green and blue. The images thereby obtained are also called RGB images. However, the image capturing device can alternatively also have any other combination of different color channels such as, for example, "Cyan" "Magenta," "Yellow" and the "Key" black percentage, whereby images in the so-called CMYK color spectrum are obtained. Alternatively or additionally, it is preferential for the image capturing device to have a resolution of the intensity values, particularly of the different color values, of at least 100, in particular at least 200 intensity values. For example, a resolution of 8 bits, which corresponds to 256 different intensity values, is provided for each of the channels. The images obtained or respectively evaluated by means of one or more of the aforementioned configurations allow a particularly reliable determination of the residual blood in the dialyzer.

It is further preferential for the image capturing device to be configured to generate more than 250,000, in particular more than 1,000,000 image points (pixels) per image. Due to the high spatial resolution of the captured images thereby achieved, residual blood embedded in particular in the hollow fibers can be particularly reliably determined. In principle, however, not all of the image points of an image generated by the image capturing device need to be taken into account in the image analysis. In fact, it is possible to accordingly analyze only a detail of an image. If the image capturing device yields an image of approximately 1,000,000 image points, for instance, an image detail of only approximately 500,000 image points can for example be subjected to a statistical image analysis if, for example, the relevant image information, for example the filter or a representative detail of the filter, is rendered in the image detail. That saves computing capacities without compromising the reliability of the residual blood determination.

In principle, the images produced by the image capturing device can be individual frames, image sequences and/or even moving images, in particular video sequences.

It is further preferential for the control device to be configured to determine the residual blood information on the basis of a distribution of the frequency, in particular a histogram, of the intensity values in the at least one image. Generally speaking, a histogram can visualize the distribution of an image's brightness values, whereby the individual frequencies of the occurring of the gray values or respectively color values are plotted as bars along an axis representing the value range of these gray values or respectively color values. The higher the bar above a gray value or respectively color value, the more frequently this gray value or respectively color value appears in the image. The distribution of the frequency or respectively histogram of the intensity values used in the present determination of residual blood does not, however, necessarily need to be visualized, it can instead only contain the corresponding data pairs (gray value or respectively color value and absolute frequency or respectively relative frequency) for the distribution of the in particular absolute or relative statistical frequency of the gray value or respectively color value in an image. In the case of an image taken by an image capturing device having two or more color channels, the statistical analysis of the image preferably accordingly takes into account two or more individual color channel histograms, e.g. three histograms with an RGB image and four histograms with a CMYK image.

The control device is preferably additionally configured to determine the residual blood information on the basis of at least one parameter which characterizes a characteristic of the distribution of the frequency of the intensity values in the at least one image. By means of the preferably automatically determined parameter of the frequency distribution of the gray values or respectively color values of an image, any residual blood in the dialyzer or filter respectively can be determined with even greater reliability. This also applies in particular to one or more of the following parameters included as examples.

Preferably, the at least one parameter contains or respectively characterizes the expected value of the intensity values or respectively the centroid of the distribution of the frequency of the intensity values respectively in the at least one image, in particular the expected value or centroid of the color values in the blue and/or green wavelength range or, respectively, the blue and/or green channels in the at least one image. The expected value preferably indicates the intensity value at which the centroid of an area formed by the distribution of the frequency of the intensity values above the abscissa (x-axis) lies. Preferably, the control device is to that end configured to determine the residual blood information characterizing the content, in particular an amount, of residual blood in the dialyzer on the basis of the expected value or respectively centroid as determined.

Alternatively or additionally, the at least one parameter contains or respectively characterizes an intensity value at which the distribution of the frequency of the intensity values exhibits a maximum. Alternatively or additionally, the at least one parameter contains or respectively characterizes an intensity value at which the distribution of the frequency of the intensity values is divided into two equal areas.

Preferably, the at least one parameter characterizes the width of the distribution of the frequency of the intensity values in the at least one image. In particular, the at least one parameter characterizes at least one of the following: the standard deviation of the intensity values from the expected value and/or the variance of the intensity values and/or a range between two intensity values (cut-on, cut-off) at which the progression of the distribution of the frequency exceeds and/or reaches a preset threshold, in particular zero. On the basis of the parameter characterizing the width of the distribution, the control device can reliably automatically determine whether a filter is uniformly colored or if there are white areas without blood deposits and/or the filter exhibits streaking in order to derive the residual blood information from same. Alternatively, however, the residual blood information can also be derived directly from the width of the distribution.

Preferably, the at least one parameter characterizes the slope of the distribution of the frequency of the intensity values in the at least one image, in particular of the color values in the red wavelength range or red channel respectively. In particular, the control device is configured to determine the residual blood information characterizing the content, in particular an amount, of residual blood in the dialyzer on the basis of the slope of the distribution particularly for the red wavelength range. Particularly thereby examined is whether the distribution of the frequency is skewed to the right or skewed to the left, whereby concluded in the case of a right-skewed distribution is a white filter without appreciable blood deposits and concluded with a left-inclined distribution is a filter containing blood deposits.

Preferably, the at least one parameter characterizes the kurtosis of the distribution of the frequency of the intensity values. The kurtosis is preferably a measure of the sharpness or peakedness of a distribution, in particular relative to a normal distribution. If, for example, there are several peaks or shoulders along the progression of the distribution of the frequency, then the kurtosis value decreases. Preferably, the control device is configured to determine the residual blood information characterizing the content, in particular an amount, of residual blood in the dialyzer on the basis of the kurtosis, whereby able to be concluded in particular in the case of a lower value of the kurtosis is a white filter without appreciable blood deposits and able to be concluded with a higher value of the kurtosis is a filter containing a corresponding amount of residual blood.

Preferably, the residual blood information determination further includes a factoring in of calibration data as determined in a calibration process which comprises the following steps: capturing images of two or more dialyzers, in particular of filters within the dialyzers containing different amounts of residual blood, and generating corresponding image data having a plurality of image points, each of which associated with at least one intensity value, in particular a color value, and generating calibration data based on information on the respective differing amounts of residual blood contained in the dialyzers and an analysis of the statistical frequency of at least part of the intensity values in the respectively captured images.

In the calibration process preferably occurring prior to the actual determining of the residual blood information, multiple images, e.g. 5, 10 or 20 images, are preferably captured at different locations and/or under different conditions, e.g. different rotational positions, of the respective dialyzer or respectively filter containing a respectively known amount of residual blood. For example, images are taken of three differently filled dialyzers, e.g. filled only with NaCl solution (without blood), filled completely with blood and, respectively, only filled halfway with blood. Each image data taken of the differently filled dialyzers undergoes an evaluation which determines the statistical frequency of the intensity values respectively occurring in the images, in particular of different color values such as for instance in the red, green and blue color channels, and preferably characterizes by means of at least one of the above-described parameters such as, for example, the expected value, the width, slope and/or kurtosis of the respective distribution of the frequency of the color values.

For example, for each of the differently filled dialyzers, the calibration data incorporates at least one parameter or corresponding intensity value respectively for each color channel. With for example three different dialyzers (only NaCl, half-filled with blood, completely filled with blood) and for example three color channels (red, green, blue), three expected values of the red, green and blue color values are obtained per dialyzer.

This calibration data can then be used when later determining residual blood in a dialyzer in the case of an unknown amount of residual blood by determining the expected value of the color values in the red, green and blue color channels of the image captured of the dialyzer and comparing it to the color value triplet obtained for the differently filled dialyzers of the calibration data. Alternatively, it is also possible to determine or respectively compare the expected values of the color values from only two color channels or only one color channel. It was thus surprisingly found that determining the expected value for the green color channel and comparing it to the expected values for the green color channel obtained in the calibration on differently filled dialyzers enables a particularly simple and nevertheless reliable determination of the residual blood in the respective dialyzer.

Figure 2:
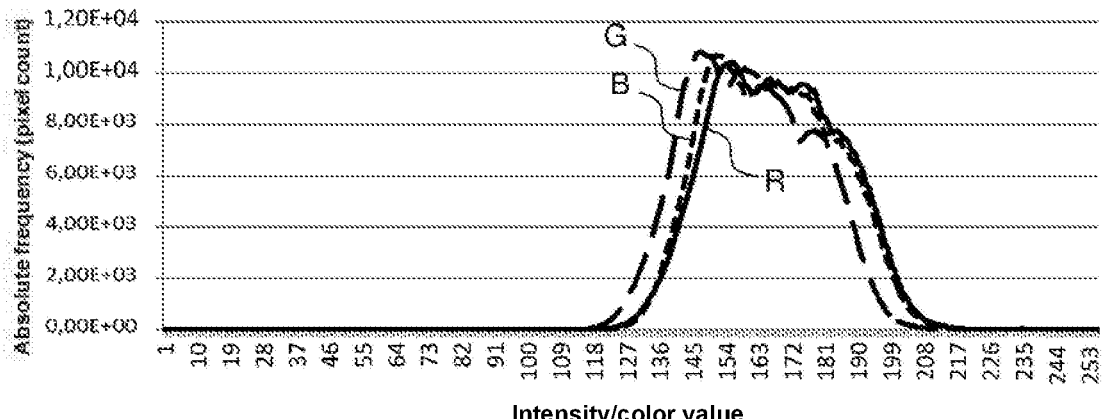
Figure 3:
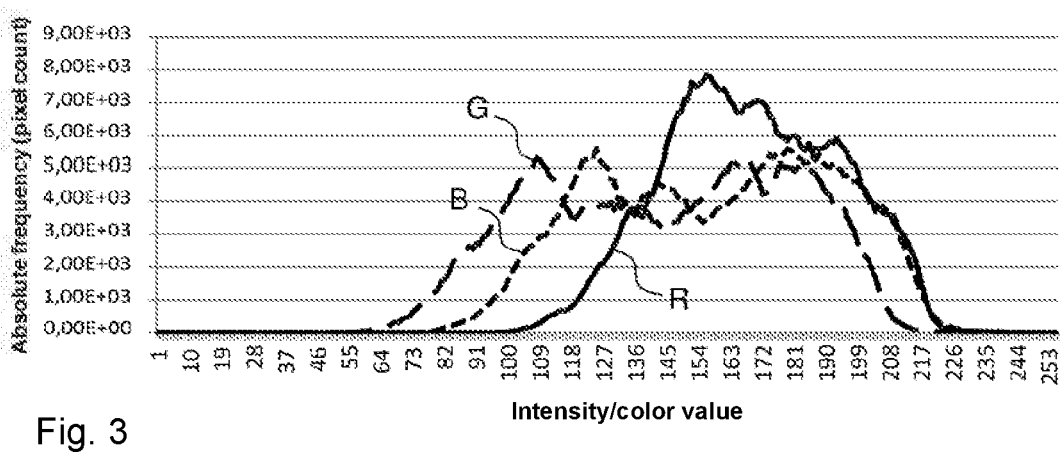
Figure 4:
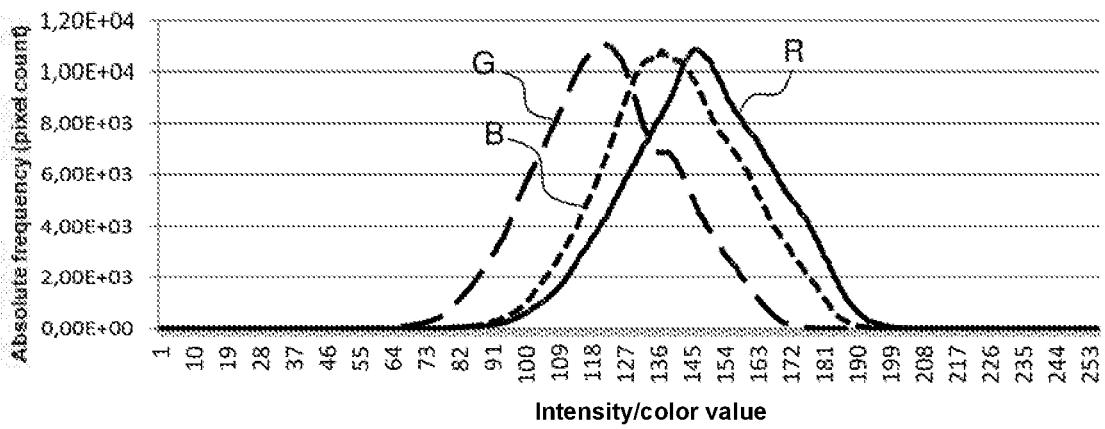
Figure 5:
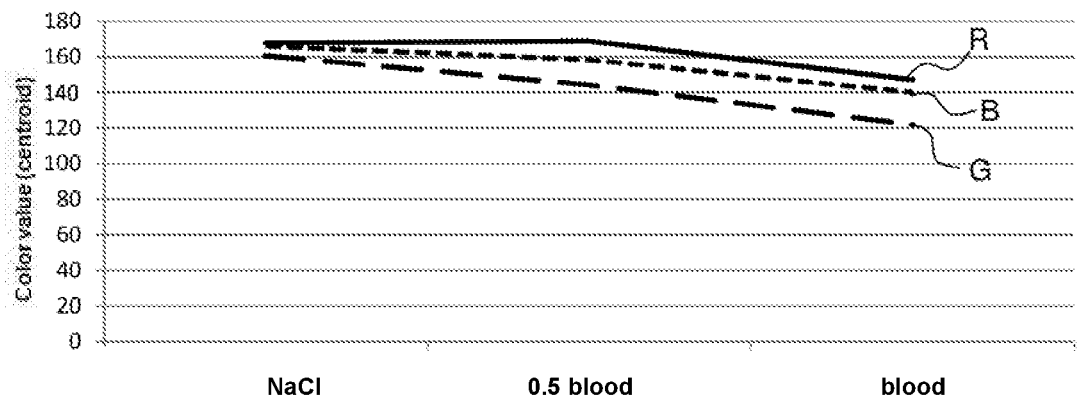

Further advantages, features and possible applications of the present invention are yielded by the following description in conjunction with the figures. Shown are:

FIG. 1 one example of a device for determining residual blood in a dialyzer;

FIG. 2 a first example of a distribution of the frequency of intensity values in an image of a dialyzer filled with NaCl; and FIG. 3 a second example of a distribution of the frequency of intensity values in an image of a dialyzer filled halfway with blood;

FIG. 4 a third example of a distribution of the frequency of intensity values in an image of a dialyzer filled completely with blood;

FIG. 5 a graphic representation of one example of calibration data; and

Figure 6:
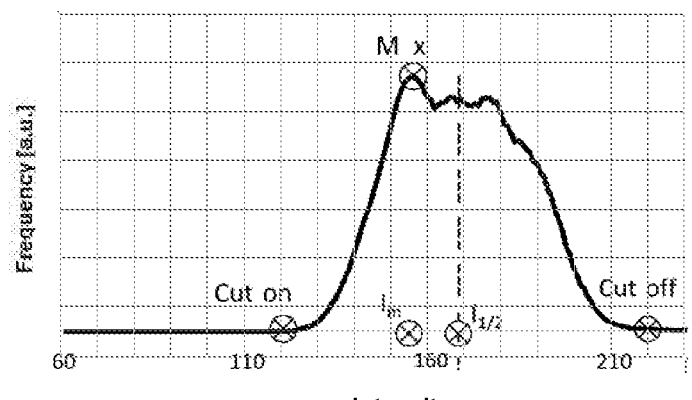

FIG. 6 a graphic representation to illustrate different parameters for characterizing a distribution of the frequency of intensity values.

FIG. 1 shows an example of a device 1 for determining residual blood in a dialyzer 2 in a schematic side view. The dialyzer 2 comprises a substantially cylindrical shell 3 of a preferably transparent material such as for instance plastic or glass. On both ends of the shell 3, there are provided end caps 5 at which respective connectors 5a and 5b are located, at which blood and dialysate can be conducted into or respectively out of the interior of the dialyzer 2 when they are connected to corresponding connectors of a dialysis device 10 by (not shown) tubes.

A filter 4 is located within the dialyzer 2, or shell 3 respectively, which in the depicted example comprises a plurality of only schematically indicated hollow fibers of a semipermeable material. During the dialysis procedure, the blood to be cleansed is conducted inside the hollow fibers while they are flushed from the outside with dialysate.

In the depicted example, the dialyzer 2 is situated—e.g. after finishing a dialysis procedure or after being separated from the dialysis device 10 respectively—in a holding device comprising two bearing elements 6 having semi-cylindrical recesses in which the dialyzer 2 is in particular rotatably mounted.

An image capturing device 7, for example a still-frame and/or video camera, is provided in the interior of one of the bearing elements 6, depicted in cross section, which is capable of taking one or more images of a detail of the dialyzer 2 or the filter 4 respectively in the region of the bearing element 6. Preferably, a camera chip serves as the image capturing device 7.

Preferably, an illumination device 8 is further provided, e.g. one or more light emitting diodes, by means of which the relevant detail of the dialyzer 2 or respectively filter 4 is illuminated at least during the capturing of the image.

A rotatable mounting of the dialyzer 2 in the bearing elements 6 can provide for multiple images of the dialyzer 2 to be successively taken at different rotational positions. The taking of a panoramic image can in particular be provided for by rotating the dialyzer 2.

The image capturing device 7 is preferably designed to capture color images and has, for example, three color channels in the red (R), green (G) and blue (B) wavelengths or respectively wavelength ranges.

Each image of the dialyzer 2 or respecitvely filter 4 taken by the image capturing device 7 has a plurality of image points, so-called pixels, each associated with at least one intensity value, in particular three different color values for the R, G and B color channels.

The image data generated by the image capturing device 7 is fed to a control device 9 and analyzed there in order for conclusions to be able to be drawn about any residual blood in the filter 4.

At least part of the color values are thereby analyzed in terms of their frequency, in particular in terms of their frequency distribution, in the respective image and corresponding residual blood information derived therefrom which indicates whether or respectively how much residual blood is present in the filter 4.

The residual blood information can be solely of a qualitative nature, e.g. "residual blood present"/"no residual blood present" or else contain quantitative information on the residual blood content, e.g. in the form of a rough indication of the residual blood content (e.g. "high," "average," "low") and/or also even be in the form of numerical values (e.g. weight percent, volume percent, absolute concentration values, information on the so-called streaking of the filter).

The residual blood information is preferably determined in consideration of at least one parameter characterizing at least one characteristic of the frequency distribution of at least one of the color values. Preferably, predetermined calibration data, in which one or more characteristics of the frequency distribution is/are correlated with the blood content, is thereby additionally factored in. This will be described in greater detail in the following.

FIG. 2 shows a first example of a distribution of the frequency of intensity values in an RGB image of a dialyzer filled with NaCl. The graphic representation depicted is a so-called histogram in which the absolute frequency in the form of the number of image points (so-called pixel count) in the respectively captured image is plotted over the intensity values or respectively color values occurring in the image in the individual red (R), green (g) and blue (B) color channels.

FIG. 3 shows a second example of a distribution of the frequency of intensity values in an RGB image of a dialyzer filled halfway with blood. In contrast to the color value distributions in the different channels shown in FIG. 2, the distributions in FIG. 3 are broader. The distributions among the different R, G and B channels also show greater differentiation than in FIG. 2.

FIG. 4 shows a third example of a distribution of the frequency of intensity values in an image of a dialyzer completely filled with blood. In contrast to the color value distributions in the different channels shown in FIGS. 2 and 3, the distributions in FIG. 4 are more symmetrical and considerably sharper. Furthermore, a clear shift of the so-called centroid of the distributions is discernible in the different R, G and B channels.

In the context of calibrating the device 1, or the corresponding method respectively, the centroid of the frequency distributions can for example be determined and correlated with the respective blood content. The position of the centroid $x_s$ of a distribution f(x) along the x-axis is defined as follows:

$$x_s = \frac{\int_a^b x \cdot f(x) dx}{\int_a^b f(x) dx} = \frac{I_1}{I_2}$$

To perform a calculation with discrete intensity values (x-axis) and frequency values (y-axis), the equation is adjusted as follows:

$$x_s = \frac{\sum_{i=0}^{255} \int_{x_i}^{x_{i+1}} x \cdot f(x) dx}{\sum_{i=0}^{255} \int_{x_i}^{x_{i+1}} f(x) dx} = \frac{I_1}{I_2}$$

Then obtained is:

with $f(x) \{x \in \mathbb{R} \mid x_i \leq x \leq x_{i+1}\} = const = Fw(i)$ $$I_1 = \sum_{i=0}^{255} \left[\frac{1}{2} \cdot Fw(i) \cdot x \right]_{x_i}^{x_{i+1}} = \sum_{i=0}^{255} \frac{1}{2} Fw(i) \cdot (x_{i+1}^2 - x_i^2)$$

with $x_{i+1} = x_i + 1$ $$I_1 = \sum_{i=0}^{255} \frac{1}{2} Fw(i) \cdot (x_{i+1}^2 - x_i^2) = \sum_{i=0}^{255} \frac{1}{2} Fw(i) \cdot ((x_i + 1)^2 - x_i^2)$$

$$I_1 = \sum_{i=0}^{255} \frac{1}{2} Fw(i) \cdot (x_i^2 + 2x_i + 1 - x_i^2)$$

$$I_1 = \sum_{i=0}^{255} Fw(i) \cdot \left(x_i + \frac{1}{2}\right)$$

$$I_2 = \sum_{i=0}^{255} [Fw(i) \cdot x]_{x_i}^{x_{i+1}} = \sum_{i=0}^{255} Fw(i) \cdot (x_i + 1 - x_i)$$

$$I_2 = \sum_{i=0}^{255} Fw(i)$$

$$x_s = \frac{\sum_{i=0}^{255} Fw(i) \cdot \left(x_i + \frac{1}{2}\right)}{\sum_{i=0}^{255} Fw(i)}$$

This equation corresponds to a determination of the centroid from the (absolute) histogram data. It is also possible to determine the centroid $x_s$ from (relative) histogram data:

$$x_s = \sum_{i=0}^{255} Fw(i) \cdot h_n(i)$$

$h_n$ = relative frequency

A determination of the centroid is also possible from raw pixel data:

$$x_s = \bar{x} = \frac{1}{i} \sum_{i=0}^{255} p(i)$$

$p(i)$: pixel count $\{p \in \mathbb{R} \mid 0 \leq x \leq 255\}$

A correlation can in this way be made between the intensity/color value in the respective centroid on the one hand and the different dialyzer blood fillings on the other from the distributions of the different color values shown as examples in FIGS. 2 to 4.

The calibration data thereby obtained for a specific dialyzer/filter type is illustrated graphically in FIG. 5. As is apparent from the illustration, the centroid intensity values obtained for the green (G) color channel vary particularly markedly as a function of the respective blood content. The same also applies, although in somewhat less pronounced form, to the blue (B) color channel.

Therefore, when determining the residual blood in such a dialyzer, preferably the frequency distribution, or the respective centroid, is identified for the green and/or blue and/or red color channel. By comparing the intensity value of the centroid thereby obtained to the calibration data for the green and/or blue and/or red color channel, a conclusion can then be drawn as to the residual blood content in the dialyzer. Using the green color channel is preferential.

Preferably, the intensity value and blood content value pair respectively obtained in the calibration, as shown in FIG. 5, is linearly interpolated and/or extrapolated so that the residual blood content can also be determined for amounts of blood which are between, below and/or above the amounts of blood considered in the calibration.

Alternatively or additionally, it is also possible to accordingly determine the respective centroid of the frequency distributions shown in FIGS. 2 to 4 along the y-axis (frequency) and incorporate same into the determination of residual blood. In this case, a correlation between the, in particular absolute, frequency of the intensity values and the blood content is accordingly made in the calibration procedure.

While the centroid of the distributions along the x-axis represents a measure of the blood content-dependent shift of the frequency distributions of the intensity values, the centroid along the y-axis characterizes their weighting.

Alternatively or additionally to the centroid or expected value respectively, however, other characteristics of the frequency distributions can also be considered in the residual blood determination / calibration such as, for example, the width, slope and/or kurtosis of the respective distribution, the intensity value or color value at which the frequency distribution exhibits a maximum and/or the intensity values, so-called cut-on/cut-off values, at which the respective distribution passes out of or respectively again reaches the zero line.

FIG. 6 shows a graphic representation of an image's frequency distribution of intensity values to illustrate different parameters for the characterizing of the distribution characteristics.

The dashed line drawn at intensity value $I_{1/2}$ divides the area formed by the frequency distribution over the x-axis into two equal areas. The intensity value $I_{1/2}$ can, alternatively or additionally to the centroid/expected value, likewise be used in the determining of residual blood.

The two "cut-on" and "cut-off" points characterize the intensity and/or frequency values over the course of the frequency distribution at which the intensity exceeds or again reaches the zero value. The corresponding intensity values can, alternatively or additionally to the above-described parameters, likewise be used in the determining of residual blood.

The same also applies accordingly to the "Max" point, which characterizes the most frequently occurring intensity value $I_{max}$ or, respectively, the frequency of said intensity value $I_{max}$.

The invention claimed is:

1. A device for determining residual blood in a dialyzer comprising
   a holding device configured to accommodate the dialyzer,
   an image capturing device configured to capture at least one image of the dialyzer accommodated by the holding, and generate corresponding image data having a plurality of image points, each of which assigned at least one respective intensity value, and
   a control device configured to determine residual blood information characterizing the presence and/or content of residual blood in the dialyzer on the basis of a statistical frequency of at least a portion of the intensity values in the at least one image.

2. The device according to claim 1, wherein
   the image capturing device is configured to capture electromagnetic radiation at two or more different wavelengths and generate intensity values, for each of the wavelengths per each image point, and
   the control device is configured to determine the residual blood information on the basis of a statistical frequency of the intensity values for one or more of the wavelengths in the at least one image.

3. The device of claim 2, wherein said intensity values are two or more color values.

4. The device according to claim 1, wherein the control device is configured to determine the residual blood information on the basis of a distribution of the frequency, of the intensity values in the at least one image.

5. The device according to claim 4, wherein the control device is configured to determine the residual blood information on the basis of at least one parameter characterizing a characteristic of the distribution of the frequency of the intensity values in the at least one image.

6. The device according to claim 5, wherein the at least one parameter is given by the expected value of the intensity values and/or the centroid of the distribution of the frequency of the intensity values.

7. The device according to claim 5, wherein the at least one parameter is given by an intensity value ($I_{max}$) at which the distribution of the frequency of the intensity values exhibits a maximum.

8. The device according to claim 5, wherein the at least one parameter is given by an intensity value ($I_{max}$) at which the distribution of the frequency of the intensity values is divided into two equal areas.

9. The device according to claim 5, wherein the at least one parameter characterizes the width of the distribution of the frequency of the intensity values.

10. The device according to claim 9, wherein the at least one parameter characterizes at least one of the following:
    the standard deviation of the intensity values from the expected value,
    the variance of the intensity values,
    a range between two intensity values (cut-on, cut-off) at which the progression of the distribution of the frequency exceeds and/or reaches a preset threshold, in particular zero.

11. The device according to claim 5, wherein the at least one parameter characterizes the slope of the distribution of the frequency of the intensity values.

12. The device according to claim 5, wherein the at least one parameter characterizes the kurtosis of the distribution of the frequency of the intensity values.

13. The device of claim 4, wherein said distribution of the frequency is a histogram.

14. A dialysis system comprising
    the device according to claim 1 and
    a dialysis device able to be connected to the dialyzer by tubes and configured to conduct blood and dialysate through the dialyzer to cleanse the blood.

15. The device according to claim 1, wherein said holding device is a filter located in the dialyzer.

16. The device of claim 1, wherein said intensity value is a color value.

17. A method for determining residual blood in a dialyzer, comprising the following steps:
    capturing at least one image of the dialyzer, in particular a filter (II) located in the and generating corresponding image data having a plurality of image points, each of which assigned at least one respective intensity value, and determining residual blood information characterizing the presence and/or content of residual blood in the dialyzer on the basis of a statistical frequency of at least a portion of the intensity values in the at least one image.

18. The method according to claim 17, wherein the residual blood information is further determined in consideration of calibration data obtained by a calibration process which comprises the following steps:

capturing images of two or more dialyzers, and generating corresponding image data having a plurality of pixels, each of which associated with at least one intensity value, and generating calibration data based on information on the respective different amounts of residual blood contained in the dialyzers and an analysis of the statistical frequency of at least part of the intensity values in the respectively captured images.

19. The method of claim 17, wherein said at least one image of the dialyzer is an image of a filter located in the dialyzer, and the intensity value is a color value.

20. The method of claim 18, wherein said images of two or more dialyzers are images of filters located within the two or more dialyzers containing different amounts of residual blood, and the at least one intensity value is at least one color value.

* * * * *

UNITED STATES PATENT AND TRADEMARK OFFICE
CERTIFICATE OF CORRECTION

PATENT NO. : 11,890,400 B2
APPLICATION NO. : 17/043709
DATED : February 6, 2024
INVENTOR(S) : Erlenkoetter et al.

Page 1 of 1

It is certified that error appears in the above-identified patent and that said Letters Patent is hereby corrected as shown below:

In the Claims

Claim 1, Column 9, Lines 59-60, "by the holding, and generate" should read -- by the holding device, and generate --

Claim 17, Column 10, Lines 66-67, the phrase ", in particular a filter (II) located in the" should be deleted Signed and Sealed this
Twenty-sixth Day of March, 2024

Katherine Kelly Vidal
*Director of the United States Patent and Trademark Office*